(12) United States Patent
Stefan et al.

(10) Patent No.: US 8,753,031 B2
(45) Date of Patent: Jun. 17, 2014

(54) HOLDING DEVICE FOR MEDICAL INSTRUMENTS

(75) Inventors: Jochen Stefan, Wald (DE); Uwe Bacher, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 244 days.

(21) Appl. No.: 12/975,005

(22) Filed: Dec. 21, 2010

(65) Prior Publication Data

US 2011/0150561 A1    Jun. 23, 2011

(30) Foreign Application Priority Data

Dec. 23, 2009 (DE) .......................... 10 2009 060 493

(51) Int. Cl.
*F16C 11/00* (2006.01)

(52) U.S. Cl.
USPC .......... 403/135; 403/76; 403/165; 248/181.1; 248/288.51

(58) Field of Classification Search
USPC ......... 403/53, 57, 76, 77, 122, 127, 129, 135, 403/137, 138, 144–146, 164–166; 248/181.1, 181.2, 288.31, 288.51
See application file for complete search history.

(56) References Cited

U.S. PATENT DOCUMENTS

| | | | | |
|---|---|---|---|---|
| 2,707,645 A * | 5/1955 | Moskovitz | ...................... | 403/38 |
| 2,767,004 A * | 10/1956 | Ashworth et al. | .............. | 403/36 |
| 2,859,983 A * | 11/1958 | May | .................. | 285/90 |
| 2,861,501 A * | 11/1958 | Strelakos | ...................... | 359/802 |
| 3,584,822 A | 6/1971 | Oram | | |
| 4,034,574 A | 7/1977 | Kuder | | |
| 4,767,231 A | 8/1988 | Wallis | | |
| 4,974,802 A * | 12/1990 | Hendren | ..................... | 248/181.1 |
| 4,986,688 A * | 1/1991 | Tuan et al. | ..................... | 403/127 |
| 6,315,486 B1 * | 11/2001 | Lunz | ............................. | 403/127 |
| 6,568,871 B2 * | 5/2003 | Song et al. | .................... | 403/170 |
| 6,767,153 B1 * | 7/2004 | Holbrook | ........................ | 403/56 |
| 6,840,697 B1 * | 1/2005 | Dorr | ............................. | 403/138 |
| 7,007,901 B2 * | 3/2006 | Kondo | ............................ | 248/75 |
| 7,640,617 B2 * | 1/2010 | Kennedy et al. | ............. | 15/144.1 |
| 2002/0014567 A1 | 2/2002 | King et al. | | |
| 2004/0218352 A1 | 11/2004 | Hilman et al. | | |
| 2009/0072107 A1 | 3/2009 | Wilson et al. | | |

FOREIGN PATENT DOCUMENTS

| | | |
|---|---|---|
| DE | 854100 C | 10/1952 |
| DE | 29521305 U1 | 12/1996 |
| DE | 60216733 T2 | 11/2007 |
| WO | 0178617 A2 | 10/2001 |

OTHER PUBLICATIONS

European Search Report; Application No. EP 10 01 5161; Apr. 13, 2011; 6 pages.

* cited by examiner

*Primary Examiner* — Gregory Binda
*Assistant Examiner* — Nahid Amiri
(74) *Attorney, Agent, or Firm* — St. Onge Steward Johnston & Reens LLC

(57) ABSTRACT

A holding device for medical instruments with a bracket on which at least one medical instrument can be affixed and with at least one joint to position the bracket and/or the medical instrument, so that the at least one joint is configured as a ball and socket joint that is equipped with at least one bearing shell and one pivot ball and whose pivot angle around the longitudinal axis of the joint is restricted by a pivot guard. The pivot guard is positioned inside the pivot ball to provide a holding device for medical instruments whose pivot guard allows for a compact structure of the ball and socket joint.

9 Claims, 3 Drawing Sheets

HOLDING DEVICE FOR MEDICAL INSTRUMENTS

CROSS-REFERENCE TO RELATED APPLICATIONS

The present application claims priority of German patent application No. 10 2009 060 493.6 filed on Dec. 23, 2009, the content of which is incorporated herein by reference.

FIELD OF THE INVENTION

The invention relates to a holding device for medical instruments with a bracket on which at least one medical instrument can be affixed and with at least one joint to position the bracket and/or the medical instrument, such that the at least one joint is configured as a ball and socket joint provided with at least one bearing shell and one pivot ball whose pivoting angle around the longitudinal axis of the joint is restricted by a pivot guard.

BACKGROUND OF THE INVENTION

Holding devices of this type are often required in performing surgical procedures in order to hold medical instruments of many kinds, such as retractors, video cameras or endoscopes, in a certain position for an extended period. Because of the jointed configuration of the holding devices it is possible for the surgeon to precisely position the medical instrument held by the bracket and to secure the selected position of the holding device by blocking the joint or joints of the bracket.

To be able to supply electric current and/or a pneumatic or hydraulic pressure means to the medical instruments affixed on the holding device, and/or parts of the holding device itself such as the locking devices to secure and release the joints of the bracket, it is standard practice in the art to direct lines through the interior of the bracket and also through the joints that removably connect the bracket parts with one another.

A generic holding device with lines fed through the ball and socket joint is known, for example, from DE 295 21 305 U1. To protect the lines from becoming twisted or otherwise damaged by the pivoting motion of the joints, the ball and socket joints of this known holding device comprise a pivot guard by which the pivoting angle of the joints around their longitudinal axis can be restricted, for example prevented from pivoting by more than 360 degrees. This known pivot guard consists of a surrounding groove configured in the pivot ball as well as a pivot guard ring that is positioned on the pivot ball at a right angle to the surrounding groove and is mounted in the surrounding groove by pins pointing radially inward. As a result, a movement of the pivot ball, by the pins engaging in the surround groove, generates a pivoting movement of the pivot guard ring around the longitudinal axis of the joints. To restrict the pivot angle, a pin is positioned at a distance toward the outside and, in the event of pivoting by the guard ring, comes into contact with a guard pin configured as a backstop, which in turn is firmly mounted in the bearing shell of the ball and socket joint.

With this known structure it is possible to restrict the pivot angle of the joint in such a way that the lines fed through the joint are protected; however, this known structure also has the problem that, in the event of diagonal movements of the pivot ball, in particular with simultaneous pivoting movement around the longitudinal axis of the joint, the system can jam or the joints can become stiff through friction of the pins on the surface of the pivot ball or of the pivot guard ring in the guide track. In addition this known structure has the disadvantage of requiring considerable construction space around the pivot ball.

Consequently it is the object of the invention to provide a holding device for medical instruments of the aforementioned type whose pivot guard makes possible a compact structure of the ball and socket joint.

SUMMARY OF THE INVENTION

This object is fulfilled according to the invention in that the pivot guard is positioned in the interior of the pivot ball.

By moving the pivot guard into the interior of the pivot ball according to the invention, it becomes possible to provide an especially compactly formed ball and socket joint whose pivot guard in addition is protected from impacts from outside.

According to this practical embodiment of the invention it is proposed that the pivot guard should consist of a stop that is firmly connected with the pivot ball and a counterstop that is firmly connected with the joint housing. As soon as the stop positioned on the pivot ball comes up against the counterstop positioned on the joint housing, the pivoting ability of the ball and socket joint is blocked in order to protect the lines fed through the joint from damage.

It is further proposed with the preferred embodiment of the invention that, to position the pivot guard inside the pivot ball, a funnel-shaped recess should be configured, widening radially toward the outside, in the part of the pivot ball surrounded by the bearing shell, in such a way that the angle of opening of the funnel-shaped recess should preferably correspond to the angle of opening of the bearing shell to the outside in order to avoid influencing the pivoting ability of the ball and socket joint.

To position and configure the stop on the pivot ball side, it is proposed with the invention that the stop should be configured approximately at the height of the center of the pivot ball on the inside of the recess. According to a preferred practical embodiment of the invention, the stop is configured as a ring embedded in the inside of the recess and a protrusion pointing radially inward.

According to a practical embodiment of the invention, the counterstop on the joint housing side, which forms the counterpart to the stop on the pivot ball side, is positioned on a rod, wherein the rod is firmly connected with the joint housing and extends inward into the recess of the pivot ball.

The rod affixed to the housing and the counterstop positioned on the rod are configured in such a way that the free end of the rod, positioned in the pivot ball, is of spherical configuration and the counterstop is configured as a stud running in the direction of the longitudinal axis of the rod and standing radially outward from the spherical free end of the rod.

With the pivot guard in assembled state, the spherical free end of the rod is advantageously positioned inside the ring equipped with the stop, in such a way that the inner diameter of the ring is of such dimensions that, apart from the shape-adapted and radially inward-pointing stop, it is larger than the outer diameter of the spherical rod end including the counterstop that stands apart in the outer direction.

It is finally proposed with a preferred embodiment of the invention that the counterstop should be configured as a spring disk that can be inserted into a groove of the rod.

Further properties and advantages of the invention can be seen from the related drawings in which an embodiment of an inventive holding device for medical instruments is presented only by way of example, without restricting the invention to this embodiment.

DETAILED DESCRIPTION OF THE INVENTION

Figure 1:
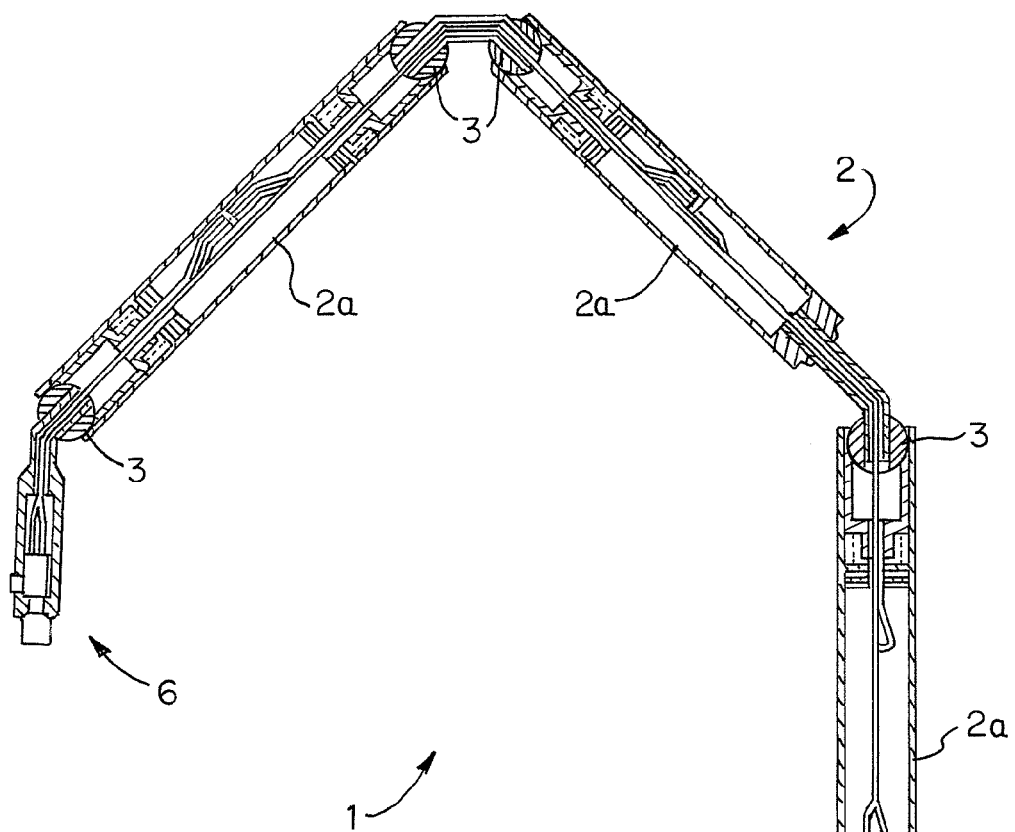
FIG. 1 shows a holding device for medical instruments according to the state of the art.

FIG. 1 shows a holding device 1 for medical instruments according to the state of the art.

This holding device 1 consists essentially of a bracket 2 consisting of several bracket parts 2a, where the individual bracket parts 2a of the bracket are connected with one another by joints 3 configured as ball and socket joints 3 so that they can pivot with respect to one another.

This type of holding device 1 is often required in executing surgical procedures in order to hold medical instruments of a number of types, such as retractors, video cameras or endoscopes, in a certain position for an extended period. Because of the jointed configuration of the holding device 1 it is possible for the surgeon to precisely position the medical instrument and to secure the selected position of the holding device 1 by blocking the joint 3 or joints 3. Besides in endoscopic surgery, holding devices 1 of this type also find applications in open surgery, i.e. in invasive procedures.

In the area of its proximal end, the bracket 2 can be affixed, for example to the operating table 5, by a jig 4. On the distal end the bracket 2 comprises an instrument insertion 6 for holding the medical instrument that is to be positioned by means of the holding device 1.

Alternatively to the structure of the bracket 2, as shown in FIG. 1, made up of several successively coupled bracket parts 2a that are connected with one another by a joint 3, it is also possible of course to configure the bracket 2 of several arms in such a way that several bracket parts 2a extend out in various directions from one joint 3. These bracket parts 2a in turn can again be coupled by a joint 3 with other bracket parts 2a and each can be equipped on its digital end with instrument insertions 6 to hold the medical instruments that are to be positioned in the holding device 1.

Figure 2:
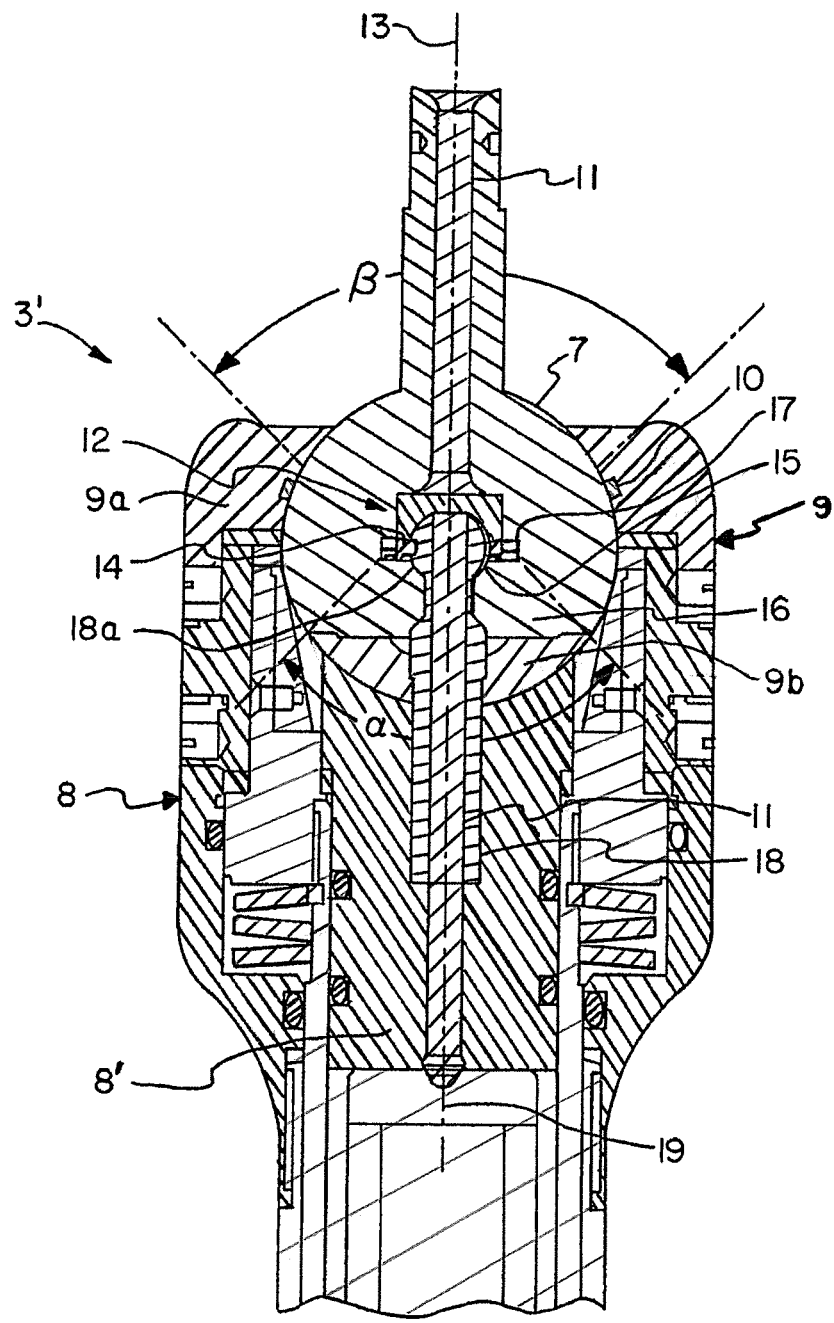
FIG. 2 shows a sectional depiction of a ball and socket joint for an inventive holding device for medical instruments.
Figure 3:
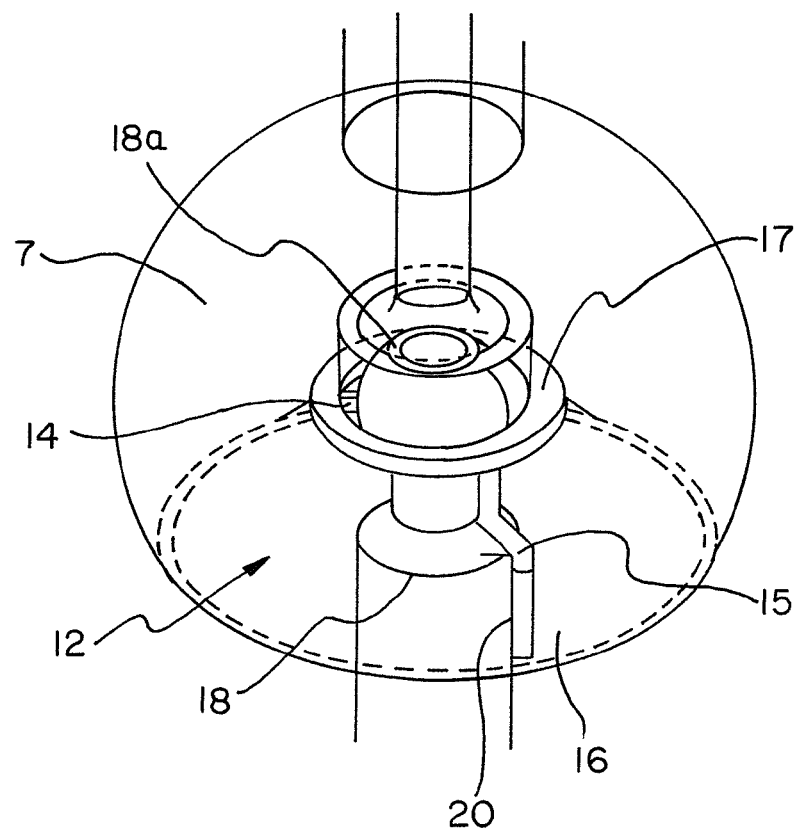
FIG. 3 shows a schematic perspective view of the pivot ball of the ball and socket joint according to FIG. 2.

The structure of the ball and socket joint 3' can be seen from FIGS. 2 and 3.

As seen in FIGS. 2 and 3, the ball and socket joints 3' consist of a pivot ball 7, which is mounted in a bearing shell 9 configured in a joint housing 8. In the illustrated embodiment, the bearing shell 9 is of two-part configuration consisting of an upper bearing shell 9a and a lower bearing shell 9b. The bearing shell 9 is positioned rigidly in the joint housing 8; that is, the upper bearing shell 9a and the lower bearing shell 9b, when the ball and socket joint 3' is in assembled state, are not movable relative to one another in the axial direction of the joint 3', and therefore no enlargement or reduction of the movement play of the pivot ball 7 is possible in the bearing shell 9 because of a movement of the bearing shell 9.

As can further be seen from FIGS. 2 and 3, the ball and socket joint 3' in the upper bearing shell 9a comprises an insulating element 10 that is contiguous with the pivot ball 7 in order to encapsulate the joint 3' from outside and thus from external influences such as moisture and dirt.

To be able to feed electric, pneumatic and/or hydraulic lines (not illustrated) as compactly as possible along the holding device 1 to the medical instrument held in the instrument insertion 6 and/or to blocking devices of the joints 3', guide channels 11 are configured in the joint 3' for inserting these lines. Because of the arrangement of the guide channels 11 and thus also of the lines inside the joints 3', however, there is a risk that the lines can be twisted or otherwise damaged by pivoting of the joints 3'. For this purpose the joints 3'are equipped with a pivot guard 12 by which the pivoting angle around the longitudinal axis 13 of the joints 3' can be restricted, so that the joint 3' cannot be pivoted, for example, by more than 360 degrees.

The pivot guard 12 of the illustrated ball and socket joint 3' is distinguished in that it is positioned inside the pivot ball 7 of the ball and socket joint 3', making possible an especially compact structure of the ball and socket joint 3'.

In the embodiment illustrated in FIGS. 2 and 3 the pivot guard 12 consists essentially of a stop 14 connected firmly with the pivot ball 7 and a counterstop 15 connected firmly with a housing body 8' of the joint housing 8.

To configure the pivot guard 12 inside the pivot ball 7, a funnel-shaped recess 16 that widens outward in the radial direction is configured in the part of the pivot ball 7 surrounded by the bearing shell 9, as can be seen in particular from FIG. 2. The angle of aperture alpha of the funnel-shaped recess 16 thus corresponds approximately to the angle of aperture beta of the bearing shell 9 to the outside, to ensure a perfect pivoting of the pivot ball 7 in the bearing shell 9.

The stop 14 on the pivot ball side in the illustrated embodiment is positioned on a ring 17, which is inserted into the inside of the recess approximately at the height of the center of the pivot ball 7. The stop 14 is configured on the ring 17 as a protrusion pointing radially inward that reduces the inner diameter of the ring 17 on the place of the stop 14 around the depth of the protrusion.

The counterstop 15 that forms the counterpart to the stop 14 in the illustrated embodiment is positioned on a rod 18 that is connected firmly with the joint housing 8 and that protrudes with its free end 18a into the funnel-shaped recess 16 of the pivot ball 7. The free end 18a of the rod 18 here is of spherical configuration and thus positioned in the center of the ring equipped with a stop 14 in such a way that the ring 17 concentrically surrounds the spherical free end 18a of the rod 18. The counterstop 15 is configured as a stud that runs in the direction of the longitudinal axis 19 of the rod 18 and stands apart toward the outside from the spherical free end 18a of the rod 18.

The stud that forms the counterstop 15 can, for example, be configured as a spring disk 15 inserted into a longitudinal groove 20 of the rod 18, as shown in FIG. 3.

The pivot guard 12 as hitherto described is positioned inside the pivot ball 7 of the ball and socket joint 3' in such a way that, on the one hand, because of the funnel-shaped configuration of the recess 16 the pivoting action of the ball and socket joint 3' is in no way restricted and, on the other hand, because with a pivoting of the pivot ball 7 around the longitudinal axis 13 of the joint 3', this pivoting is restricted to approximately less than 360 degrees by the pivot guard 12.

With a pivoting of the pivot ball 7 around the longitudinal axis 13 of the joint 3, the ring 17 that is firmly connected with the pivot ball 7 pivots with the pivot ball 7 freely around the spherical free end 18a of the rod 18 that is firmly connected with the joint housing 8 until the stop formed on the ring 17 comes into contact against the counterstop 15 formed on the free end 18a of the rod 18. Because of this restriction of the pivoting angle of the pivot ball 7 around the longitudinal axis 13 of the joint 3, it is guaranteed that lines positioned inside the guide channel 11 are not overwound and unwound or otherwise damaged.

A holding device configured as described hitherto for medical instruments is distinguished in that because of the moving of the pivot guard 12 into the inside of the pivot ball 7, the ball and socket joint 3' as a whole can be constructed very compactly. In addition, the described pivot guard 12 is distinguished in that it comprises no components that are permanently engaged with one another, so that no resistance of the joint 3' can result from mutual friction or the like.

What is claimed is:

1. A holding device comprising:
   a bracket adapted to affix at least one medical instrument;
   at least one joint connected to the bracket, the at least one joint positioning the bracket, whereby the at least one joint is configured as a ball and socket joint having at least one bearing shell and one pivot ball;
   a joint housing housing the at least one joint;
   a pivot guard having a portion positioned inside the pivot ball, the pivot guard restricting a pivot angle of the at least one joint around a longitudinal axis of the at least one joint; and
   a rod having one end connected firmly with the joint housing and a free end protruding into a recess of the pivot ball;
   wherein the pivot guard includes a stop connected firmly with the pivot ball and a counterstop connected firmly with the joint housing at the free end of the rod, and the counterstop is positioned within the recess.

2. The holding device according to claim 1, wherein said recess is configured in a part of the pivot ball surrounded by the bearing shell, said recess having a funnel shape that widens radially in an outward direction.

3. The holding device according to claim 2, wherein an angle of aperture (alpha) of the funnel-shaped recess corresponds to an angle of aperture (beta) of the bearing shell toward the outside.

4. The holding device according to claim 1, wherein the stop is positioned inside the recess proximate to a center of the pivot ball.

5. The holding device according to claim 4, wherein the stop is configured as a protrusion that is positioned on a ring inserted inside of the recess and that points radially inward.

6. The holding device according to claim 5, wherein the free end of the rod is positioned inside the ring that is equipped with the stop.

7. The holding device according to claim 1, wherein the free end of the rod that is positioned in the recess of the pivot ball is of spherical configuration.

8. The holding device according to claim 7, wherein the counterstop is configured as a stud that runs in a direction of a longitudinal axis of the rod and stands radially outward from the free end of the rod.

9. The holding device according to claim 8, wherein the counterstop is configured as a spring disk that is inserted into a longitudinal groove of the rod.

* * * * *